United States Patent
Panchapakesan et al.

(10) Patent No.: US 8,134,026 B2
(45) Date of Patent: Mar. 13, 2012

(54) PROCESS FOR THE PREPARATION OF CILASTATIN AND SODIUM SALT

(75) Inventors: Ganapathy Panchapakesan, Chennai (IN); Nagappan Arumugam, Chennai (IN); Pandi Suresh Pandian, Chennai (IN); Gollapalli Venkateswara Rao, Secundrabad (IN); Subramaniam Ganesan, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 896 days.

(21) Appl. No.: 12/084,760

(22) PCT Filed: Nov. 3, 2006

(86) PCT No.: PCT/IB2006/003092
§ 371 (c)(1),
(2), (4) Date: Jul. 9, 2008

(87) PCT Pub. No.: WO2007/054771
PCT Pub. Date: May 18, 2007

(65) Prior Publication Data
US 2009/0143614 A1    Jun. 4, 2009

(30) Foreign Application Priority Data
Nov. 9, 2005 (IN) .......................... 1636/CHE/2005

(51) Int. Cl.
C07C 319/28 (2006.01)
C07C 319/14 (2006.01)
C07C 233/46 (2006.01)

(52) U.S. Cl. ........................................ 562/506; 562/557

(58) Field of Classification Search ........................ None
See application file for complete search history.

(56) References Cited

U.S. PATENT DOCUMENTS

| 4,616,038 A | 10/1986 | Kahan et al. |
| 5,147,868 A | 9/1992 | Graham et al. |
| 2004/0152780 A1 | 8/2004 | Kumar et al. |
| 2005/0119346 A1 | 6/2005 | Kumar et al. |

FOREIGN PATENT DOCUMENTS

| EP | 0 048 301 A1 | 3/1982 |
| WO | WO 03/018544 A1 | 3/2003 |
| WO | WO 2006/022511 A1 | 3/2006 |

OTHER PUBLICATIONS

D. Graham et al. J Med Chem. 1987, 30, 1074-1090.*

* cited by examiner

*Primary Examiner* — Daniel Sullivan
*Assistant Examiner* — Yevegeny Valenrod
(74) *Attorney, Agent, or Firm* — Oliff & Berridge, PLC

(57) ABSTRACT

The present invention relates to an improved process for the preparation of Cilastatin Sodium of formula (I). The present invention also provides an isolation technique for Cilastatin acid from the reaction mixture.

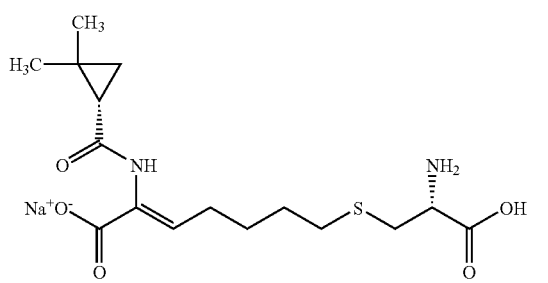

(I)

4 Claims, No Drawings

PROCESS FOR THE PREPARATION OF CILASTATIN AND SODIUM SALT

FIELD OF THE INVENTION

The present invention relates to an improved process for the preparation of Cilastatin of formula (I) and its sodium salt. The present invention also provides a direct isolation technique for Cilastatin acid from the reaction mixture.

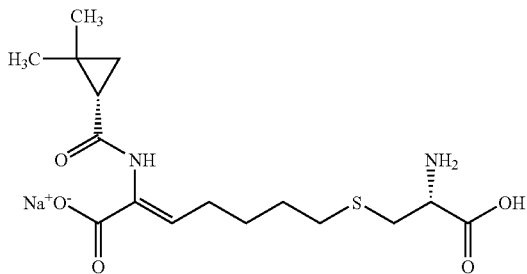

DESCRIPTION OF THE PRIOR ART

Cilastatin sodium is the sodium salt of a derivatized heptenoic acid. Its chemical name is [R—[R*,S*-(Z)]]-7-[(2-amino-2-carboxyethyl)thio]-2-[[(2,2-dimethylcyclopropyl)carbonyl]amino]-2-heptenoic acid, monosodium salt. It is an off-white to yellowish-white, hygroscopic, amorphous compound. PRIMAXIN (Imipenem and Cilastatin) is a formulation of Imipenem (a thienamycin antibiotic) and Cilastatin sodium.

Imipenem with Cilastatin acts as an effective antibiotic for the treatment of infections of various body systems. PRIMAXIN is a potent broad-spectrum antibacterial agent for intramuscular administration. Imipenem can be further described as a semi-synthetic thienamycin that is administered intravenously or intramuscularly in combination with Cilastatin to reduce toxicity. Cilastatin, a renal dipeptidase inhibitor, inhibits the enzymatic breakdown of Imipenem and increases urinary excretion of the active drug.

Originally Cilastatin was disclosed in U.S. Pat. No. 5,147,868. This patent also discloses various processes for the preparation of Cilastatin, particularly example 19A of this patent disclose a process for the preparation of Cilastatin. According to this example the condensation of 7-chloro-2-oxoheptanoic acid ethyl ester (I) with (S)-2,2-dimethylcyclopropanecarboxamide (II) by means of p-toluene sulphonic acid in refluxing toluene gives (S)-7-chloro-2-(2,2-dimethylcyclopropanecarboxamido)-2-heptenoic acid ethyl ester (III), which is hydrolyzed in aq. NaOH to yield the corresponding carboxylic acid (IV). Finally, this compound is condensed with (R)-cysteine (V) by means of NaOH in water to afford the target Cilastatin, followed by isomerisation to at 3.0 pH. The process followed in this example is depicted as below:

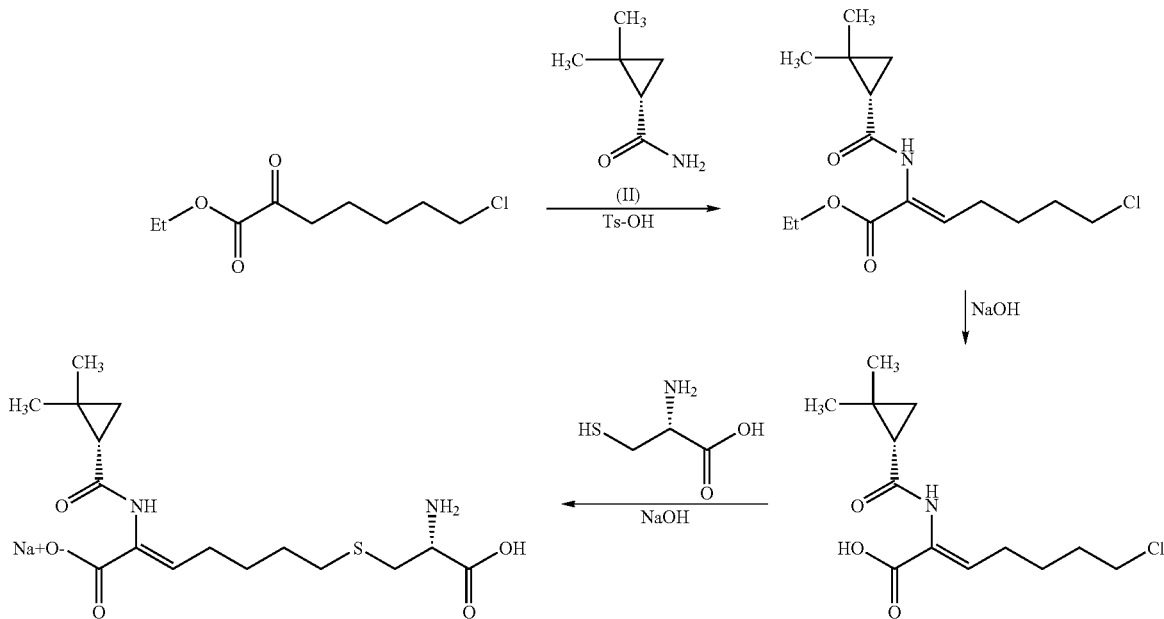

WO 03/018544 claims a process for the purification of Cilastatin, which comprises contacting a solution of crude Cilastatin with a non-ionic adsorbent resin and recovering pure Cilastatin from a solution thereof. This publication also claims a process for the isomerisation of Cilastatin by heating a solution of Cilastatin containing the corresponding E isomer at a pH of about 0.5 to 1.5. This invention not suitable for plant point of view as it involves column chromatography.

US 2004/0152780 claims a process for the preparation of pure Cilastatin sodium in an amorphous form which comprises recovering Cilastatin sodium from a solution thereof which contains an organic solvent, homogeneous mixture of organic solvents, or homogeneous mixture of organic solvents and water, by solvent precipitation. According to this patent the pure Cilastatin sodium in amorphous form was recovered from the solution of Cilastatin sodium in a solvent (where Cilastatin sodium was soluble) by adding an anti-solvent (where Cilastatin sodium was insoluble).

WO 2006/022511 claims a process for preparing Cilastatin sodium via Cilastatin amine salt, also the said patent claims Cilastatin ammonium salt. However EP 0 048 301 page 2; line 33-37 & U.S. Pat. No. 4,616,038 col 36; 40-44 anticipates the claim of the said publication. Also this patent utilizes the column chromatography for removing sodium chloride.

However taking the consideration the commercial importance of Cilastatin sodium and Imipenem, there remains a need of convenient process. Hence, we focused our research to find an alternative processes and succeeded with a process that eliminates the foregoing problems associated with earlier processes.

OBJECTIVE OF THE INVENTION

The primary objective of the present invention is to provide a commercial process for the preparation of Cilastatin.

Another objective of the present invention is to provide a process for the preparation Cilastatin sodium with high purity and in good yields.

Still another objective is to provide a process which obviates the use of chromatography and provides direct isolation of Cilastatin.

Yet another objective of the present invention provides a process for the isomerisation of 7-chloro-2-[[(1S)-2,2-dimethylcyclopropane]carboxamide]-2-heptenoic acid.

SUMMARY OF THE INVENTION

Accordingly, the present invention provides an improved process for preparation of Cilastatin or its salt of formula (I)

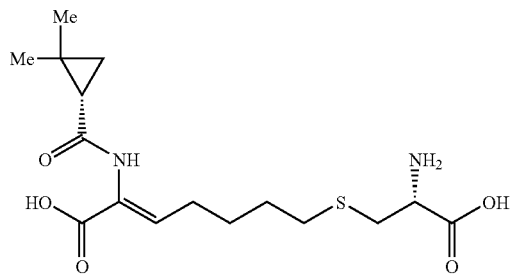

which comprises the steps of:
(i) condensing 7-chloro-2-[[(1S)-2,2-dimethylcyclopropane]carboxamide]-2-heptenoic acid of general formula (II) with L-Cysteine in the presence of base in water or an alcoholic solvent or aqueous alcoholic solvent, and
(ii) acidifying and isolating the Cilastatin acid (I).

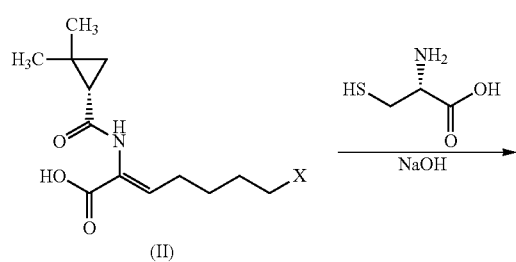

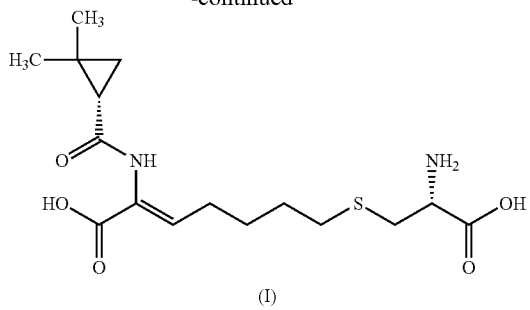

wherein X represents a leaving group selected from chloro or bromo.

Another embodiment of the present invention provides a process for the preparation of Cilastatin Sodium
a) dissolving Cilastatin acid in a solvent using an organic base,
b) adding sodium salt of weak acid, and
c) isolating Cilastatin Sodium.

The present invention further provides an improved process for the preparation of pure Cilastatin Acid of formula (I), which comprises the steps of:
i) condensing 7-chloro-2-[[(1S)-2,2-dimethylcyclopropane]carboxamide]-2-heptenoic acid of formula (I) with L-Cysteine in the presence of base an alcoholic solvent or aqueous alcoholic solvent,
ii) optionally removing NaCl or KCl by filtration and concentrating filtrate,
iii) optionally adding water,
iv) adjusting pH to 2.0 to 4.0,
v) optionally extracting the Cilastatin acid into $C_4$-$C_8$ alcohol selected form group comprising of n-butanol, cyclohexanol, and
vi) isolating Cilastatin acid.

DETAILED DESCRIPTION OF THE INVENTION

In an embodiment of the present invention, the base used in step (i) is selected from sodium hydroxide, potassium hydroxide, sodium carbonate and the like, and alcoholic solvent used in step (i) is selected from methanol, ethanol, iso-propanol and the like. It has been found that the condensation of compound of formula (II) with L-Cysteine in the alcoholic solvent medium yields Cilastatin in pure form, wherein the impurity formation is negligible.

In still another embodiment of the present invention, the L-Cysteine used in step (i) is in the form of L-Cysteine hydrochloride monohydrate or R-Cysteine hydrochloride or L-Cysteine hydrobromide monohydrate.

In another embodiment of the present invention, the pH of reaction mass is adjusted to 2.0 to 4.0 using hydrochloric acid, sulfuric acid, formic acid, acetic acid, trifluoracetic acid and the like.

In another embodiment of the present invention, there is provided a process for isolation/crystallization of Cilastatin acid without utilizing the column chromatography, which crystallizing Cilastatin from a solution thereof which contains an water miscible organic solvent, water, or a mixture thereof.

According to this invention the aqueous solution of Cilastatin containing impurities which may be inorganic salts such as sodium chloride, sodium bromide, sodium formate, sodium acetate and the like, or organic impurities which may have formed due to the degradation of Cilastatin, or the side products formed during the synthesis, or unreacted intermediates is stirred at a pH in the range of 4.0 to 2.0 for a long period, the solid crystallized was filtered and if required subjected to purification.

In another aspect the inorganic salts like NaCl, KCl is filtered form the reaction mass, if the condensation taken place in an alcoholic solvent medium, prior to pH adjustment. The solution of crude Cilastatin can be directly taken from the reaction mass or may be obtained by dissolving crude Cilastatin in water and water miscible solvent. It has been noted that the conventional methods requires column chromatography to remove the inorganic salt like sodium chloride that are formed during the course of reaction, whereas the present invention provides a process in which Cilastatin is directly crystallized from the reaction mass at the pH in the range of 2.0 to 4.0 more particularly at the pH in the range of 3.0.

In one more embodiment of the present invention the Cilastatin can be precipitated from reaction mass after pH adjustment by stirring the solution for a long period or it can be extracted into solvents like $C_4$-$C_8$ alcohol selected form group comprising of n-butanol, cyclohexanol, followed by isolating Cilastatin acid form the resultant layer. In another aspect the Cilastatin acid is isolated from the $C_4$-$C_8$ alcohol layer by reducing the volume of the layer followed by filtering the precipitated Cilastatin acid, or by evaporating the layer followed by crystallizing Cilastatin acid from mixture of water and water-miscible solvent.

In yet another embodiment of the present invention, water-miscible solvent used solvent used during crystallizing Cilastatin sodium are selected from acetone, methanol, THF, n-butanol, acetonitrile, DMF, and it can be vary from 5% to 95%. In another embodiment of the present invention the Cilastatin obtained may contain up to 10% NaCl or about 0.5% NaCl, preferably 2% to 0.5% of NaCl.

In still another embodiment of the present invention, the Cilastatin obtained according to the present invention can be optionally subjected to isomerisation process by the technique known in prior art.

In still another embodiment of the present invention, the starting material 7-chloro-2-[[(1S)-2,2-dimethylcyclopropane]carboxamide]-2-heptenoic acid of formula (II) is prepared by utilizing the process available in the prior art.

In one more embodiment of the present invention, the present invention provides a process for isomerisation of E-isomer of 7-chloro-2-[[(1S)-2,2-dimethylcyclopropane] carboxamide]-2-heptenoic acid, Cilastatin precursor which comprises treating the mixture of E and Z-7-chloro-2-[[(1S)-2,2-dimethylcyclopropane]carboxamide]-2-heptenoic acid in a solvent selected from toluene, MDC, water and the like or mixtures thereof with HCl at a pH in the range of 0.5 to 4.5. The said isomerisation can be done at a temperature in the range of 10° C. to reflux temperature of the solvent, preferably room temperature i.e. 27 to 35° C.

In yet another embodiment of this present invention, the solvent used for the dissolution of Cilastatin acid is selected from ethanol, isopropanol, n-butanol, denatured sprit, acetone, THF, acetonitrile, DMF and the like or mixtures thereof. Thus present invention provides a novel process for the preparation of Cilastatin sodium. The solvent system is chosen such a way that the Cilastatin Sodium per se is insoluble in the solvent system In yet another embodiment of this present invention, the base used in step (a) is selected from DBU, DBN, DABCO, TMG, triethyl amine (TEA), DEA, diisopropyl amine, NaOH and the like.

In one more embodiment of the present invention the step (a) solution is subjected to carbon treatment (optional) and micron filtration to get the Cilastatin sodium as sterile product. Accordingly this present invention provides a process for the preparation of Sterile Cilastatin Sodium.

In still another embodiment of the present invention, the salt forming agent in step (b) is selected from sodium lactate, sodium acetate, sodium 2-ethyl hexanoate, and the like or the mixture thereof. In another embodiment of the present invention the salt forming agent can be added directly or by dissolving the salt forming agent using step (a) solvent.

The present invention is exemplified by the following examples, which are provided for illustration only and should not be construed to limit the scope of the invention.

Example 1

Preparation of 7-chloro-2-[[(1S)-2,2-dimethyl cyclopropane]carboxamide]-2-heptenoic Acid (II) (Starting Material)

To the solution of S-2,2-dimethylcyclopropyl carboxamide (100 gm) in toluene (500) was added Ethyl-7-chloro-2-oxo-heptanoate (270 gm) and p-toluene sulphonic acid (1.5 gm). The resulted solution was refluxed for 20 hrs azeotropically. The resulted mass was cooled to 5-10° C. and added the solution of sodium hydroxide (140 gm) in water 500 ml and the resulted two-layered solution was stirred for 8 hrs at 25-30° C. up to the complete disappearance of ester. The toluene layer was separated and the aqueous layer was washed with toluene. The pH of the aqueous layer was adjusted to 4.0 to 4.5 and extracted with toluene (1 lt). The toluene layer containing 7-chloro-2-[[(1S)-2,2-dimethyl cyclopropane]carboxamide]-2-heptenoic acid was washed with water and used as such for the next step. The ratio of Z and E isomer 90:10% was obtained.

Example 2

Isomerisation of 7-chloro-2-[[(1S)-2,2-dimethyl cyclopropane]carboxamide]-2-heptenoic Acid (II)

To the toluene layer, obtained from example −1, was added hydrochloric acid (1 lt) and stirred for 4 hrs at 25-30° C. till the disappearance of E isomer. The toluene layer was separated and washed with water and followed by brine. The toluene layer was distilled out under vacuum up to 50% of the original volume. To the reaction mass hexane/IPE was added at 50° C. and cooled to 0-5° C. The precipitated mass was filtered and washed with hexane (200 ml) and dried under vacuum to obtained 99% pure Z-7-chloro-2[[(1S)-2,2-dimethyl cyclopropane]carboxamide]-2-heptenoic acid (150 gm) as white solid.

Example 3

Preparation of Cilastatin Acid (I)

To the solution of sodium hydroxide (90 gm) in water (1 lt) was added L-Cysteine hydrochloride monohydrate (96 gm) and Z-7-chloro-2[[(1S)-2,2-dimethyl cyclopropane]carboxamide]-2-heptenoic acid and stirred at 25-30° C. till the disappearance of Z-7-chloro-2[[(1S)-2,2-dimethyl cyclopropane] carboxamide]-2-heptenoic acid. After completion of reaction, the reaction mass was washed with dichloromethane (500 ml). To the aqueous layer was added carbon (10 gm) and stirred and filtered. To the filtrate was added water (1 lt) and the pH of the solution was adjusted to 3.0 and stirred for 24 hrs. The precipitated mass was filtered, washed with water (200 ml) and with acetone (500 ml) and dried to obtain 10 gm white solid with 97% purity. The solid was dissolved in water (700 ml) and added MDC (700 ml) and ethyl acetate (100 ml) and stirred for 10 hrs. The precipitated mass was filtered and washed with water (100 ml) and acetone (200 ml) and dried to obtain 100 gm white Cilastatin acid with 99.5% purity.

Example 4

Preparation of Cilastatin Sodium

The Cilastatin acid (100 gm, 99.5%) was dissolved in the mixture of ethanol (2.5 lt) and triethylamine (30 gm) at 25 to 30° C. To the resulted clear solution was added carbon (10 gm) and stirred and filtered. The filtrated was filtered again through sterile micron (0.2µ) filter. To the resulted clear solution was added solution of sodium ethyl hexanoate (70 gm) in ethanol (70 ml) and stirred for 3 hrs at 25 to 30° C. The precipitated Cilastatin sodium was filtered and washed with ethanol (80 ml) and followed by acetone (200 ml) and dried under vacuum to obtained 95 gm Cilastatin sodium as amorphous white solid with 99.5% purity.

Example 5

Preparation of Cilastatin Acid

To the solution of sodium hydroxide (88 gm) in methanol (1500 ml) was added Z-7-chloro-2-[[(1S)-2,2-dimethyl cyclopropane]carboxamide]-2-heptenoic acid and stirred to dissolve. To the resulted clear solution was added L-Cysteine hydrochloride monohydrate (97 gm) and stirred the resulted suspension at 60 to 65° C. till the disappearance of Z-7-chloro-2-[[(1S)-2,2-dimethyl cyclopropane]carboxamide]-2-heptenoic acid. After completion of reaction, the pH insoluble salts were filtered. The filtrate was distilled out under vacuum. The residue was dissolved in water (500 ml) and washed with dichloromethane (500 ml). The pH of aqueous layer was adjusted to 3 to 4 from the original pH in the range of 5.5, and with n-butanol (500 ml). The butanol layer was washed with water and distilled. The residue was dissolved in water (100 ml) and added acetonitrile (1500 ml) at 50° C. and further refluxed at 80° C. for one hr. The precipitated cilastatin acid was filtered and washed with acetonitrile (100 ml). The crude wet cake (60 gm) was refluxed with acetonitrile water mixture (9:1, 1500 ml), and cooled to yield 60 gm pure cilastatin acid with 99.5% purity.

Example 6

Preparation of Cilastatin Acid

To the solution of sodium hydroxide (88 gm) in methanol (1500 ml) was added Z-7-chloro-2-[[(1S)-2,2-dimethyl cyclopropane]carboxamide]-2-heptenoic acid and stirred to dissolve. To the resulted clear solution was added L-Cysteine hydrochloride monohydrate (97 gm) and stirred the resulted suspension at 60 to 65° C. till the disappearance of Z-7-chloro-2-[[(1S)-2,2-dimethyl cyclopropane]carboxamide]-2-heptenoic acid. The pH of the reaction mass was adjusted to 7.0 with conc.HCl and filtered the insoluble salts. The filtrated was distilled out under vacuum. The residue was dissolved in water (500 ml) and washed with dichloromethane (500 ml). The pH of aqueous layer was adjusted to 3 to 4 from the original pH in the range of 5.5, and with n-butanol (500 ml). The butanol layer was washed with water and distilled up to 50% of original volume and stirred at 25° C. The precipitated cilastatin acid was filtered and washed with n-butanol (100 ml) followed by acetone to yield 60 gm pure cilastatin acid with 99.7% purity.

Example 7

Preparation of Cilastatin Sodium

The Cilastatin acid (100 gm, 99.5%) was dissolved in the mixture of n-butanol (2.5 lt) and triethylamine (30 gm) at 25 to 30° C. To the resulted clear solution was added carbon (10 gm) and stirred and filtered. The filtrated was filtered again through sterile micron (0.2µ) filter. To the resulted clear solution was added solution of sodium ethyl hexanoate (70 gm) in n-butanol (70 ml) and stirred for 3 hrs at 25 to 30° C. The precipitated Cilastatin sodium was filtered and washed with n-butanol (80 ml) and followed by acetone (200 ml) and dried under vacuum to obtained 80 gm Cilastatin sodium as amorphous white solid with 99.78% purity.

Abbreviations;
DBU: diazabicyclo[5,4,0]undec-7-en
DBN: 1,5-diazabicyclo[4,3,0]-non-5-ene
TMG: 1,1,3,3-tetramethylguanidine
DABCO: 1,4-diazabicyclo-[2,2,2]-octane

We claim:
1. An improved process for the preparation of Cilastatin Acid of formula (I),

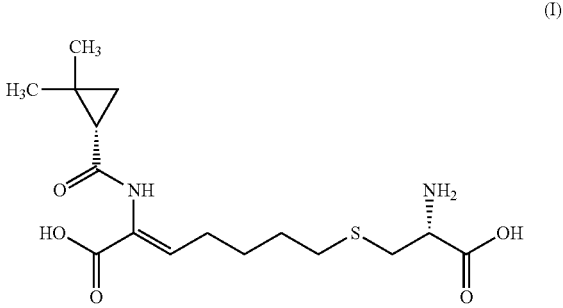

the process comprises the steps of:
i) condensing 7-chloro-2-[[(1S)-2,2-dimethylcyclopropane]carboxamide]-2-heptenoic acid of formula (II)

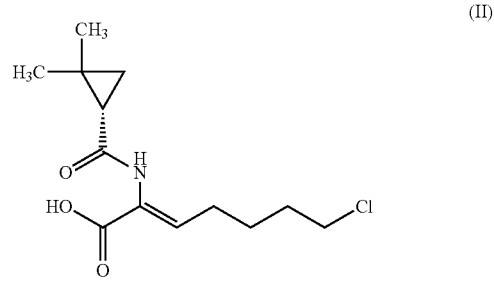

with L-Cysteine in the presence of a base and an alcoholic solvent or an aqueous alcoholic solvent;
ii) optionally removing inorganic salts by filtration and concentrating filtrate;
iii) optionally adding water;
iv) adjusting pH to 2.0 to 4.0;
v) extracting the Cilastatin acid into $C_4$-$C_8$ alcohol selected from the group consisting of n-butanol and cyclohexanol; and
vi) isolating Cilastatin acid.

2. A process as claimed in claim 1, wherein the isolation of Cilastatin acid is carried out by reducing the $C_4$-$C_8$ alcohol to half of the original volume, followed by filtration.

3. A process as claimed in claim 1, wherein the isolation of Cilastatin acid is carried out by concentrating the $C_4$-$C_8$ alcohol layer, followed by crystallizing the solid.

4. A process as claimed in claim 1, wherein the alcoholic solvent used in step (i) is selected from methanol, ethanol, iso-propanol, or n-butanol; and base used in step (i) is selected from sodium hydroxide, potassium hydroxide, or sodium carbonate.

\* \* \* \* \*